US006884874B2

(12) United States Patent
Eldridge et al.

(10) Patent No.: US 6,884,874 B2
(45) Date of Patent: Apr. 26, 2005

(54) PROCESS AND INTERMEDIATES

(75) Inventors: Ann M. Eldridge, King of Prussia, PA (US); Johann Hiebl, Linz (AT)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/390,252

(22) Filed: Mar. 17, 2003

(65) Prior Publication Data

US 2004/0014980 A1 Jan. 22, 2004

Related U.S. Application Data

(62) Division of application No. 10/009,381, filed as application No. PCT/US01/28443 on Sep. 12, 2001, now Pat. No. 6,570,024.
(60) Provisional application No. 60/231,784, filed on Sep. 12, 2000.

(51) Int. Cl.$^7$ ................................................ C07K 17/06
(52) U.S. Cl. ................................................... 530/391.9
(58) Field of Search ....................................... 530/391.9

(56) References Cited

U.S. PATENT DOCUMENTS

| 5,208,020 | A | * | 5/1993 | Chari et al. | ............... | 424/181.1 |
| 6,333,410 | B1 | * | 12/2001 | Chari et al. | ................. | 540/456 |
| 6,441,163 | B1 | * | 8/2002 | Chari et al. | ................. | 540/458 |
| 6,573,074 | B1 | * | 6/2003 | Fulston et al. | .............. | 435/119 |

* cited by examiner

*Primary Examiner*—Mary E. Ceperley
(74) *Attorney, Agent, or Firm*—Andreas V. Lockenour; Edward R. Gimmi

(57) ABSTRACT

Processes for preparing N-methyl-L-alanine derivatives and novel intermediates of the process. The derivatives and intermediates are useful for preparing cell-binding agent/maytansinoid complexes.

4 Claims, No Drawings

PROCESS AND INTERMEDIATES

RELATED APPLICATIONS

This application is a divisional application of U.S. application Ser. No. 10/009,381 filed Dec. 3, 2001 now U.S. Pat. No. 6,570,024, which claims benefit to International Application PCT/US01/28443, filed Sep. 12, 2001 which claims benefit from Provisional Application No. 60/231,784 filed Sep. 12, 2000.

FIELD OF THE INVENTION

The present invention relates to a process for producing N-methyl-L-alanine derivatives and to novel process intermediates.

BACKGROUND OF THE INVENTION

Processes for the preparation of N-methyl-L-alanine derivatives from dithioalkanoic acid intermediates and N-methyl-L-alanine have been reported in U.S. Pat. No. 5,208,020. The compounds are useful for linking cytotoxic maytansinoids to cell-binding agents such as antibodies. Antibody/maytansinoid complexes are useful as tumor-activated pro-drugs.

For example, the multi-step synthesis of N-methyl-N-(3-methyldithio-propanoyl)-L-alanine has been disclosed. First, 3-methyldithiopropanoic acid was prepared by adding methyl methanethiosulfonate in ethanol to a solution of 3-mercaptopropanoic acid in water. After extraction, washing and concentration, the 3-methyldithiopropanoic acid was isolated by distillation. Isobutylchloroformate and triethylamine were added to the 3-methyldithiopropanoic acid in THF to form the corresponding mixed anhydride as intermediate. Subsequently, a mixture of N-methyl-L-alanine and triethylamine in water was added. After extraction, oncentration and chromatography, a 34% yield of N-methyl-N-(3-methyldithio-propanoyl)-L-alanine was obtained.

A major shortcoming of the prior art processes is the necessity of two chromatography steps to remove side products from the desired reaction products. Further, the use of isobutylchloroformate in the reaction scheme allows for racemization which leads to a final product containing the undesired D-enantiomer. Thus, there is a need in the art for improved methods to prepare N-methyl-L-alanine derivatives with an optical purity >95% enantiomeric excess (ee) where the intermediates are more stable, resulting in less undesired side products.

SUMMARY OF THE INVENTION

One aspect of the invention is processes for the preparation of N-methyl-L-alanine derivatives.

Another aspect of the invention is novel intermediates useful for the preparation of N-methyl-L-alanine derivatives.

Another aspect of the invention is processes for the preparation of the novel intermediates of the invention.

Yet another aspect of the invention is cell-binding agent/maytansinoid complexes prepared from the N-methyl-L-alanine derivatives or novel intermediates produced by the processes of the invention.

DETAILED DESCRIPTION OF THE INVENTION

All publications, including but not limited to patents and patent applications, cited in this specification are herein incorporated by reference as though fully set forth.

By the term "coupling reagent" as used herein and in the claims is meant a compound or compounds which are capable of forming an activated derivative of methyldithiopropionic acid or its homologues which is stable to hydrolysis under the employed reaction conditions and yields a compound of Formula I with an optical purity >95% ee when reacted with N-methyl-L-alanine.

The present invention provides a process for the preparation of compounds of Formula I (I)

[Structure showing HO-C(=O)-CH-N(-C(=O)-LSZ) where L is]

$$-\overset{R_1}{\underset{|}{CH}}-M-(CH_2)_a- \quad \text{or} \quad -(CH_2)_d-\bigcirc-$$

where
R$_1$ is H, methyl or ethyl;
M is a direct bond, CH$_2$, $$-\overset{CH_3}{\underset{|}{CH}}-, \quad \text{or} \quad -\overset{CH_2CH_3}{\underset{|}{CH}}-;$$

a is 0 or an integer of 1 to 9 when M is a direct bond provided that when M is one or more carbon atoms a is 0 or an integer of 1 to 8;
d is an integer of 3 to 8; and
Z is H or SR$_2$, where R$_2$ is linear alkyl, branched alkyl, cyclic alkyl, aryl, substituted aryl or heterocyclic.

The present invention also provides novel intermediates that are useful in the process of the invention.

The present invention also provides antibody/maytansinoid complexes produced by the process of the invention.

The process of the invention comprises the steps of reacting a salt of a mercaptoalkanoic acid of Formula II (II)

[Structure: HO-C(=O)-LSH]

where L is as defined above;
and thiolsulfonates of Formula III $$QSO_2SQ \quad \text{(III)}$$

where Q is H, linear alkyl, branched alkyl, cyclic alkyl, aryl, substituted aryl or heterocyclic,
in a disulfide formation reaction where a salt of a compound of Formula II in water is added to a compound of Formula III in a water-immiscible polar organic solvent to form intermediates of Formula IV (IV)

[Structure: HO-C(=O)-LSSQ]

where L and Q are as defined above; and reacting a compound of Formula IV in an esterification reaction with a coupling reagent such as that of Formula V

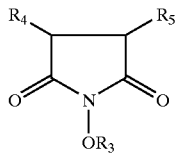
(V)

where $R_3$ is H or substituted uronium salt of the formula

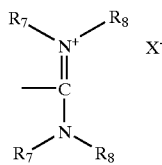

where $X^-$ is $PF_6^-$ or $BF_4^-$, $R_7$ and $R_8$ are independently linear alkyl, branched alkyl, cycloalkyl or $(CH_2)_e$ where e is an integer of 3 to 8 with the proviso that when $R_7$ is $(CH_2)_e$, $R_8$ is a direct bond, or a substituted phosphonium salt of the formula

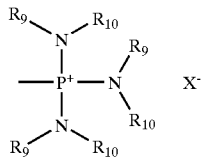

where $X^-$ is $PF_6^-$ or $BF_4^-$, $R_9$ and $R_{10}$ are independently linear alkyl, branched alkyl, cycloalkyl or heterocyclic; and $R_4$ and $R_5$ are independently H, a double bond, linear alkyl, branched alkyl, cyclic alkyl, aryl, substituted aryl or heterocyclic.

If $R_3$ is H, the reaction is carried out in the presence of a carbodiimide reagent of Formula VI

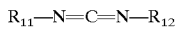
$R_{11}$—N=C=N—$R_{12}$ (VI)

where $R_{11}$ and $R_{12}$ are independently linear alkyl, branched alkyl, cyclic alkyl, aryl, substituted aryl or heterocyclic. Preferably, the carbodiimide reagent of Formula VI is 1-[3-(dimethylamino)propyl]-3-ethylcarbodiimide hydrochloride (EDCI.HCl) where $R_{11}$ is ethyl and $R_{12}$ is dimethylaminopropyl or 1,3-dicyclohexylcarbodiimide (DCC) where $R_{11}$ and $R_{12}$ are cyclohexyl. Particularly preferred is EDCI.HCl.

Alternatively, if $R_3$ is a uronium or phosphonium salt, the reaction is carried out in the presence of a base, preferably triethylamine or diisopropylethylamine.

These reactions form compounds of Formula VII

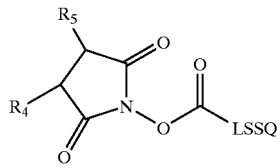
(VII)

where $R_4$, $R_5$, L and Q are as defined above.

Compounds of Formula VII are activated esters and are novel intermediates of the process of the invention and are stable to hydrolysis under the employed reaction conditions and allow racemization-free coupling with N-methylalanine. Preferably, the compounds are crystalline.

Compounds of Formula VII are subsequently reacted with N-methyl-L-alanine (Formula VIII)

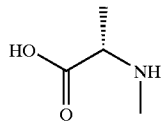
(VIII)

to form a compound of Formula I.

Further, the present invention also includes a process for the preparation of compounds of Formula I comprising reacting a compound of Formula VII with N-methyl-L-alanine to form a compound of Formula I and compounds of Formula I prepared by the process.

The present invention also includes a process for the preparation of a compound of Formula VII

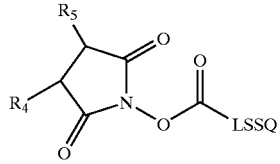
(VII)

where $R_4$ and $R_5$ are independently H, a double bond, linear alkyl, branched alkyl, cyclic alkyl, aryl, substituted aryl or heterocyclic, L is

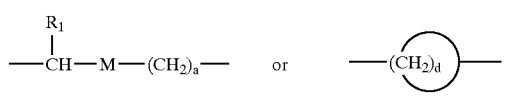

where
$R_1$ is H, methyl or ethyl;
M is a direct bond, $CH_2$,

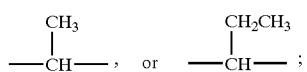

a is 0 or an integer of 1 to 9 when M is a direct bond provided that when M is one or more carbon atoms a is 0 or an integer of 1 to 8; and
d is an integer of 3 to 8; and Q is H, linear alkyl, branched alkyl, cyclic alkyl, simple or substituted aryl or heterocyclic which comprises the steps of:

(1) reacting a salt of a mercaptoalkanoic acid of Formula II

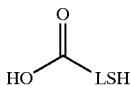  (II)

where L is as defined above;
and thiolsulfonates of Formula III $QSO_2SQ$  (III)

where Q is as defined above,
in a disulfide formation reaction where a salt of a compound of Formula II in water is added to a compound of Formula III in a water-immiscible polar organic solvent to form intermediates of Formula IV

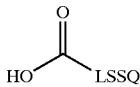  (IV)

where L and Q are as defined above; and (2) reacting a compound of Formula IV in an esterification reaction with a coupling reagent of Formula V

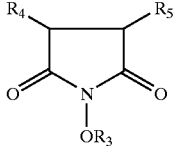  (V)

where
$R_3$ is H or substituted uronium salt of the formula

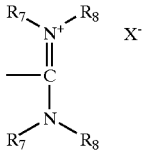

where $X^-$ is $PF_6^-$ or $BF_4^-$, $R_7$ and $R_8$ are independently alkyl, cycloalkyl or $(CH_2)_e$, where e is an integer of 3 to 8 with the proviso that when $R_7$ is $(CH_2)_e$, $R_8$ is a direct bond,
or a substituted phosphonium salt of the formula

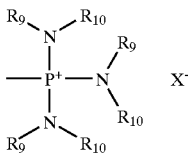

where $X^-$ is $PF_6^-$ or $BF_4^-$, $R_9$ and $R_{10}$ are independently linear alkyl, branched alkyl, cycloalkyl or heterocyclic; and
$R_4$ and $R_5$ are as defined above, provided that when $R_3$ is H, the reaction is carried out in the presence of a carbodiimide reagent of Formula VI

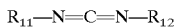  (VI)

where
$R_{11}$ and $R_{12}$ are independently linear alkyl, branched alkyl, cyclic alkyl, aryl, substituted aryl or heterocyclic, and
further provided that if $R_3$ is a uronium or phosphonium salt, the reaction is carried out in the presence of a base,
to form compounds of Formula VII.

Examples of linear alkyls include methyl, ethyl, propyl, butyl, pentyl and hexyl. Examples of branched alkyls include isopropyl, isobutyl, sec-butyl, tert-butyl, isopentyl and 1-ethyl-propyl. Examples of cyclic alkyls include cyclopropyl, cyclobutyl, cyclopentyl and cyclohexyl.

Examples of aryls include phenyl and naphthyl. Examples of substituted aryls include aryls substituted with alkyl, halogen (such as chlorine, bromine and iodine), nitro, amino, sulfonic acid, carboxylic acid, hydroxy and alkoxy.

Heteroatoms are selected from O, N and S. Examples of heterocyclics include pyrrollyl, pyridyl, furyl and thiophene.

Compounds of Formula II and their salts can be prepared by known methods from readily available starting materials such as described in U.S. Pat. No. 5,208,020.

Compounds of Formula III such as methyl methanethiolsulfonate and S-phenyl benzenethiolsulfonate can be purchased from chemical supply houses such as Aldrich Chemical Co. (Milwaukee, Wis.) or prepared from readily available starting materials by known disulfide oxidation methods such as described in Xia et al., Synth. Commun. 27, 1301–1308 (1997) and Pinnick et al., J. Org. Chem. 45, 930–932 (1980) provided that Q does not include any moieties that render inoperative the process of the invention.

Exemplary compounds of Formula V are:
N-hydroxysuccinimide (Va);
O-(N-succinimidyl)-1,1,3,3-bis(tetramethylene)uronium tetrafluoroborate or its corresponding hexafluorophosphate (Vb);
O-(N-succinimidyl)-1,1,3,3-tetramethyluronium-tetrafluoroborate or its corresponding hexafluorophosphate (Vc);
N-hydroxy-5-norbornene-2,3-dicarboxylic acid imide (Vd);
O-(5-Norbornene-2,3-dicarboximido)-1,1,3,3-tetrametyluronium tetrafluoroborate (Ve);
O-(5-Norbornene-2,3-dicarboximido)-1,1,3,3-tetrametyluronium hexafluorophosphate derivative (Vf);
N-hydroxyphthalimide (Vg);
1,1,3,3-tetramethyluronium tetrafluoroborate N-hydroxyphthalimide (Vh);
1,1,3,3-tetramethyluronium hexafluorophosphate N-hydroxyphthalimide (Vi);
N,N,N',N'-bis(pentamethylene)uronium tetrafluoroborate N-hydroxyphthalimide (Vj);
N,N,N',N'-bis(pentamethylene)uronium hexafluorophosphate N-hydroxyphthalimide (Vk);
N,N,N',N'-bis(tetramethylene)uronium tetrafluoroborate N-hydroxyphthalimide (Vl);
N,N,N',N'-bis(tetramethylene)uronium hexafluorophosphate N-hydroxyphthalimide (Vm);
N,N,N',N'-tetramethyluronium tetrafluoroborate (Vn);
N,N,N',N'-tetramethyluronium hexafluorophosphate (Vo);

tris(dimethylamino)phosphonium tetrafluoroborate (Vp);

tris(dimethylamino)phosphonium hexafluorophosphate (Vq);

tripyrrolidinophosphonium tetrafluoroborate (Vr);

tripyrrolidinophosphonium hexafluorophosphate (Vs);

1,3-dimethylimidazolidinium tetrafluoroborate (Vt); and 1,3-dimethylimidazolidinium hexafluorophosphate (Vu).

Compounds of Formula V can be purchased from chemical supply houses such as Fluka Chemical Corp. (Milwaukee, Wis.) or prepared by known methods from readily available starting materials. For example, compounds of Formula V can be prepared by the method of Knorr et al. in *Tetrahedron Lett.* 30, 1927–1930 (1989).

Compounds of Formula VI can be purchased from chemical supply houses such as Aldrich Chemical Co. (St. Louis, Mo.) or prepared by known methods from readily available starting materials.

The compound of Formula VIII (N-methyl-L-alanine) can be purchased from BACHEM Bioscience Inc. (King of Prussia, Pa.).

The reaction to convert compounds of Formula II to compounds of Formula IV is carried out by adding an aqueous solution of a salt of a compound of Formula II to a compound of Formula III in a water-immiscible polar organic solvent, preferably at a temperature range of less than −5° C. Most preferably, an aqueous solution of the sodium salt of a compound of Formula II is added slowly to a solution of the compound of Formula III in tetrahydrofuran at a temperature range of about −15° C. to about −5° C. A particularly preferred temperature range is about −10° C. to about −5° C.

Preferably, the reaction to convert compounds of Formula IV to the activated esters of Formula VII, when $R_3$ of Formula V is H, is carried out in the presence of a carbodiimide reagent at a temperature range of about 0° C. to about 20° C., preferably about 0° C. to about 12° C., in a solvent such as methylene chloride. When $R_3$ of Formula V is a uronium or phosphonium salt, the reaction is carried out in the presence of a base, preferably triethylamine or diisopropylethylamine.

Preferably, the reaction to convert compounds of Formula VII to compounds of Formula I is carried out at ambient temperature in a polar solvent such as aqueous ethanol/triethylamine.

The reagents, conditions and intermediates used in the present invention provide for high yields of the desired compounds of Formula I making the process appropriate for industrial scale utilization. Further, the process of the invention has other advantages over the processes disclosed in U.S. Pat. No. 5,208,020. Specifically, the claimed process converts compounds of Formula II to compounds of Formula IV without the formation of undesired side products of symmetric disulfides of thioproprionic acid or its homologues. Accordingly, no isolation step for compounds of Formula IV is necessary and a one-pot process can be used to convert compounds of Formula II to the novel intermediates of Formula VII, which can be isolated. Alternatively, the Formula VII intermediate is not isolated and a one-pot process can be used to convert compounds of Formula II to compounds of Formula I.

Further, the claimed process affords the activated esters of Formula VII which are crystalline and stable to hydrolysis. Accordingly, the compounds of Formula I produced by the reaction of N-methyl-L-alanine with the compounds of Formula VII are substantially optically pure L-isomer.

Most preferably, the process of the present invention is used for preparing a compound of Formula Ia which is N-methyl-N-(3-methyldithiopropanoyl)-L-alanine

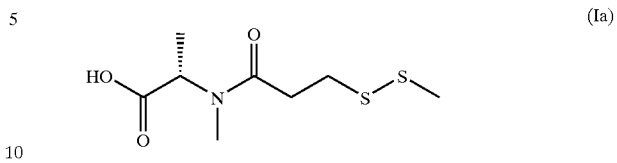

(Ia)

The preferred process is shown schematically below.

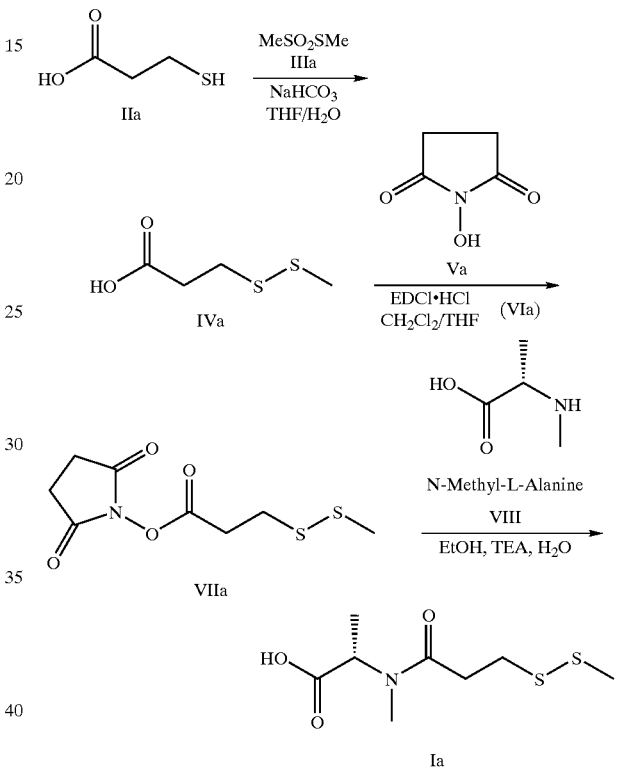

The process of the invention can be used to make cell-binding agent/maytansanoid complexes which are useful as tumor-activated pro-drugs. Compounds of Formula VII can be converted into a cell-binding agent/maytansinoid complex. Further, compounds of Formula I produced by the process of the invention are used as described in U.S. Pat. No. 5,208,020 to produce N-methyl-L-alanine containing maytansanoid derivatives. These derivatives are then conjugated to cell-binding agents, preferably antibodies, via various linkers. Preferably, the linkage is a disulfide link.

An exemplary cell-binding agent/maytansinoid complex can be prepared by a process comprising the following steps:

(1) esterifying maytansinol with a compound of Formula I prepared by the process of the invention to form a disulfide-containing maytansinoid ester;

(2) reducing the disulfide-containing maytansinoid ester prepared by step (1) to a thiol-containing maytansinoid;

(3) introducing dithiopyridyl groups into a cell-binding agent; and (4) linking the thiol-containing maytansinoid produced by step (2) to the dithiopyridyl cell-binding agent of step (3) by a disulfide link.

The present invention will now be described with reference to the following specific, non-limiting example.

EXAMPLE

Preparation of N-methyl-N-(3-methyldithiopropanoyl)-L-alanine (Ia)

All reagents utilized herein were sourced as first described below.

Step 1: Preparation of Methyldithiopropionic Acid (IVa)

A 3 L three-necked round bottom flask equipped with an overhead stirrer and thermometer was charged with 3-mercaptopropionic acid (416.6 g, 3.93 moles, 1 equiv, Aldrich Chemical Co., St. Louis, Mo.) and water (HPLC grade, 1.36 L, 1.36 kg, Burdick & Jackson, Muskegon, Mich.). Solid sodium bicarbonate (362.5 g, 4.31 mole, 1.1 equiv, Mallinckrodt, Phillipsburg, N.J.) was added at a rate to control foaming from off-gassing of carbon dioxide. The addition was endothermic and took 1 hour, the temperature decreasing from 20° C. to 10° C. A 12 L three-necked round bottom flask, equipped with an overhead stirrer, a 2 L addition funnel, a thermometer, and a nitrogen inlet was charged with methyl methanethiolsulfonate (540.0 g, 441.5 mL, 4.28 moles, 1.09 equiv, Aldrich Chemical Co.) and tetrahydrofuran (3.25 L, 2.89 kg, Burdick & Jackson) and the solution cooled with an ethylene glycol/dry ice bath to −8 to −10° C. and placed under a nitrogen atmosphere. The prepared aqueous solution of sodium mercaptopropionate was transferred to the addition funnel and added to the reaction mixture at a rate to maintain the reaction temperature at less than or equal to −5° C. On this scale the addition took 2 hours and the temperature range was −10 to −5° C. Stirring was continued in the same temperature range and after 15 minutes an HPLC in-process control assay showed the disappearance of 3-mercaptopropionic acid. After stirring for 40 minutes, aqueous hydrochloric acid (3N, 500 mL, EM Science, Gibbstown, N.J.) was added to the reaction mixture until the pH registered 3.0 to 3.5 by ColorpHast indicator strips (pH 0 to 6 range). The reaction mixture was transferred to a 6 L separatory funnel, allowed to separate for 10 minutes, and the upper organic phase isolated. The aqueous phase was returned to the 12 L reaction flask and methylene chloride (1.6 L, 2.18 kg, J. T. Baker, Phillipsburg, N.J.) was added. After stirring for 10 minutes, the phases were transferred to a 6 L separatory funnel and the bottom organic layer was separated. The organic phases were combined and transferred to a 12 L three-necked flask equipped with an overhead stirrer. Magnesium sulfate (1.33 kg) was added and after stirring for 0.5 hour, the mixture was filtered through a Buchner funnel. The solid residue was rinsed with methylene chloride (1.6 L, 2.18 kg). A Karl-Fisher assay of the combined filtrate and rinse showed 0.35% water. The filtrate was stored overnight at 15° C. An in-process HPLC impurity profile of the filtrate showed 97% methyldithiopropionic acid by area percent with no symmetrical disulfide of 3-mercaptopropionic acid present.

Step 2: Preparation of Succinimidyl-3-methyldithiopropionate (VIIa)

The methyldithiopropionic acid filtrate was transferred to a 22 L three-necked round bottom flask and cooled to 0° C. with an ice-salt bath. 1-[3-(Dimethylamino)propyl]-3-ethylcarbodiimide hydrochloride (1.28 kg, 6.68 moles, 1.7 equiv, Aldrich Chemical Co.) was added over 40 minutes through a powder funnel and a temperature rise to 10° C. was observed. N-hydroxysuccinimide (525 g, 4.56 mole, 1.16 equiv, Aldrich Chemical Co.) was added over 8 minutes through a funnel and rise in temperature of 2° C. was observed. After stirring for 1 hour at 8 to 10° C., an in-process HPLC assay showed a 66.7% conversion to succinimidyl-3-methyldithiopropionate by area percent; after 2 hours, the assay showed a 98.4% conversion. The reaction was stopped after 2.5 hours and the reaction mixture was concentrated under water aspirator pressure. The resultant syrup was transferred to a clean 22 L three-necked round bottom flask and water (8.3 L, 8.3 kg, Burdick & Jackson) was added while the mixture was stirred vigorously. After stirring for 0.5 hour at ambient temperature, the white solid that formed was filtered using a sintered glass funnel. The 1201 g wet cake was washed with water (2.1 L, 2.1 kg, Burdick & Jackson) and dried for 94 hours at 20 to 25° C. at approximately 2 torr to constant weight in a GMP vacuum oven. Drying afforded 927 g of the product succinimidyl-3-methyldithiopropionate (94.7% crude yield) as a white solid with an HPLC impurity profile showing 94.6% by area percent and an NMR spectra that was the same as a working reference.

| C, H, N Analysis: | Calculated: | C 38.54; H 4.45; N 5.62; S 25.67 |
|---|---|---|
| | Found: | C 38.20; H 4.48; N 5.58; S 25.44 |
| $^{11}$C NMR (75 MHz, CDCl$_3$): | | δ 169.0, 167.1, 31.5, 31.1, 25.6, 23.2 |

Step 3: Preparation of N-methyl-N-(3-methyldithiopropanoyl)-L-alanine (Ia)

A 22 L round bottom three-necked flask equipped with an overhead stirrer, a 2 L addition funnel, a thermometer and a nitrogen inlet was charged with succinimidyl-3-methyldithiopropionate (920 g, 3.69 mole, 1 equiv) and ethanol (200 proof, 11.0 L, 8.69 kg, Aaper, Shelbyville, Ky.). N-Methyl-L-alanine (496.8 g, 4.82 mole, 1.3 equiv, BACHEM Bioscience Corp., King of Prussia, Pa.) and water (1.1 L, 1.1 kg, Burdick & Jackson) were added at ambient temperature. The resultant white slurry was placed under nitrogen and triethylamine (1.0 L, 0.73 kg, 7.21 moles, 1.96 equiv, Aldrich Chemical Co.) was then added at a rate such that the temperature did not exceed 27° C. Addition of triethylamine on this scale took 4.25 hours. An HPLC in-process control assay after 1.75 hours of triethylamine addition showed a conversion to 80.8% N-methyl-N-(3-methyldithiopropanoyl)-L-alanine. Subsequent assays after 3 hours of addition showed a 96.1% conversion and a 99% conversion after 4.25 hours. The reaction mixture was concentrated for 16 hours using a diaphragm pump at 35 to 40° C. HPLC of the concentrate showed a later running peak assumed to be the ethyl ester of the product. Ethyl acetate (7.0 L, 6.3 kg, J. T. Baker) was added and the mixture cooled with an ice bath to 15° C. Water (3.0 L, 3.0 kg, Burdick & Jackson) was added and a 2° C. exotherm was noted. The pH, measured with ColorpHast indicator paper, was adjusted from 6.5 to 3 using aqueous hydrochloric acid (3N, 1.4 L, EM Science). The entire reaction mixture was transferred to a 12 L separatory funnel and the top organic phase isolated. The aqueous phase was returned to the reaction flask and extracted twice with ethyl acetate (2×3.0 L, 5.52 kg total, J. T. Baker). The combined organic phases were washed twice with water (2×2.0 L, 4.0 kg total, Burdick & Jackson) and transferred to a 22 L three-necked round bottom flask equipped with an overhead stirrer and thermometer. The solution was cooled with an ice bath to 15° C. and magnesium sulfate (1.25 kg, Mallinckrodt) was added and an exotherm of 10° C. was noted. After stirring for 30 minutes, the mixture was filtered through a 2 L sintered glass funnel and the residue washed with ethyl acetate (1.0 L, 0.92 kg, J. T. Baker). The filtrate was concentrated in vacuo at 30 to 35° C. under water aspirator pressure. The concentrate was slurried in hexane (3.1 L, 2.04 kg, J. T. Baker), stirred for 2 hours and filtered through a Buchner funnel. The solids were rinsed with hexane (1.0 L, 0.70 kg, J. T. Baker) and dried to constant weight in a GMP vacuum oven at 25° C. for 26 hours to afford N-methyl-N-(3-methyldithiopropanoyl)-L-alanine as a white solid, 585.5 g (66.9% uncorrected yield). An HPLC chiral assay of the product showed 99.75% L-isomer and an impurity profile showed 99.13% N-methyl-N-(3-methyldithiopropanoyl)-L-alanine.

| C, H, N Analysis: | Calculated: | C 38.54; H 4.45; N 5.62; S 25.67 |
|---|---|---|
| | Found: | C 38.20; H 4.48; N 5.58; S 25.44 |

The present invention may be embodied in other specific forms without departing from the spirit or essential attributes thereof, and, accordingly, reference should be made to the appended claims, rather than to the foregoing specification, as indicating the scope of the invention.

What is claimed is:

1. An N-methyl-L-alanine containing maytansinoid conjugated to a cell-binding agent prepared by a process comprising
   (1) coupling a compound of Formula VII;

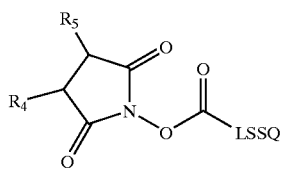

(VII)

where
R$_4$ and R$_5$ are independently H, linear alkyl, branched alkyl, cyclic alkyl, aryl, substituted aryl, heterocyclic, or R$_4$ and R$_5$ taken together form a bond
L is

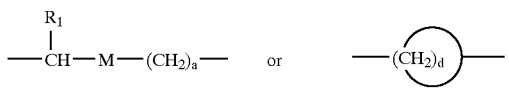

where
R$_1$ is H, methyl or ethyl;
M is a direct bond, CH$_2$,

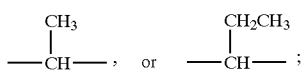

a is 0 or an integer of 1 to 9 when M is a direct bond provided that when M is one or more carbon atoms a is 0 or an integer of 1 to 8;
d is an integer of 3 to 8; and
Q is H, linear alkyl, branched alkyl, cyclic alkyl, simple or substituted heterocyclic
with N-methyl-L-alanine to form a racemization-free compound;

(2) forming an N-methyl-L-alanine containing maytansinoid with the said racemization-free compound; and (3) linking said N-methyl-L-alanine containing maytansinoid to the cell-binding agent to form a racemization-free N-methyl-L-alanine containing maytansinoid conjugated to a cell-binding agent.

2. The N-methyl-L-alanine containing maytansinoid conjugated to a cell-binding agent of claim 1 wherein the cell-binding agent is an antibody.

3. An N-methyl-L-alanine containing maytansinoid having an optical purity of greater than 95% enantiomeric excess conjugated to a cell-binding agent prepared by a process comprising the following steps:

(1) esterifying maytansinol with a compound of Formula I to form a disulfide-containing maytansinoid ester; wherein Formula I is

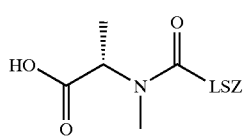

(I)

where
L is

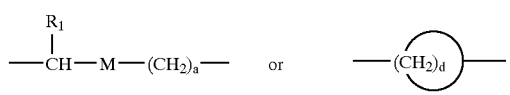

where
R$_1$ is H, methyl or ethyl;
M is a direct bond, CH$_2$,

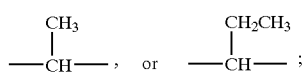

a is 0 or an integer of 1 to 9 when M is a direct bond provided that when M is one or more carbon atoms a is 0 or an integer of 1 to 8;
d is an integer of 3 to 8; and
Z is H or SR$_2$, where R$_2$ is linear alkyl, branched alkyl, cyclic alkyl, aryl, substituted aryl or heterocyclic;

(2) reducing the disulfide-containing maytansinoid ester prepared by step (1) to a thiol-containing maytansinoid;

(3) introducing dithiopyridyl groups into a cell-binding agent; and (4) linking the thiol-containing maytansinoid produced by step (2) to the dithiopyridyl cell-binding agent of step by (3) a disulfide link.

4. The N-methyl-L-alanine containing maytansinoid conjugated to a cell-binding agent of claim 3 wherein the cell-binding agent is an antibody.

* * * * *